(12) United States Patent
Rigby

(10) Patent No.: US 10,495,604 B2
(45) Date of Patent: Dec. 3, 2019

(54) METAL DETECTION APPARATUS, TESTING DEVICE AND METHOD FOR OPTIMISING A METAL DETECTION APPARATUS

(71) Applicant: Mettler-Toledo Safeline Ltd., Manchester (GB)

(72) Inventor: Paul Rigby, Bolton (GB)

(73) Assignee: METTLER-TOLEDO SAFELINE LTD., Salford, Manchester (GB)

( * ) Notice: Subject to any disclaimer, the term of this patent is extended or adjusted under 35 U.S.C. 154(b) by 330 days.

(21) Appl. No.: 15/380,803

(22) Filed: Dec. 15, 2016

(65) Prior Publication Data

US 2017/0176388 A1 Jun. 22, 2017

(30) Foreign Application Priority Data

Dec. 17, 2015 (EP) ...................................... 15200786

(51) Int. Cl.
*G01N 27/72* (2006.01)

(52) U.S. Cl.
CPC ..................................... *G01N 27/72* (2013.01)

(58) Field of Classification Search
CPC .......... G01V 3/10; G01V 3/101; G01V 3/102; G01V 3/104; G01V 3/105; G01V 3/107; G01V 3/108; G01N 27/72; G01N 27/725
See application file for complete search history.

(56) References Cited

U.S. PATENT DOCUMENTS

| 4,578,643 A * | 3/1986 | Junker | G01N 27/9086 |
|---|---|---|---|
| | | | 324/202 |
| 4,863,040 A * | 9/1989 | Sandi | B07C 5/344 |
| | | | 209/570 |
| 5,160,885 A | 11/1992 | Hannam et al. | |
| 5,994,897 A | 11/1999 | King | |
| 6,822,171 B2 | 11/2004 | Bennett et al. | |
| 8,587,301 B2 | 11/2013 | Derungs | |
| 2004/0089987 A1* | 5/2004 | Kodama | B22D 17/30 |
| | | | 266/236 |
| 2006/0060006 A1* | 3/2006 | Ornath | G01N 1/22 |
| | | | 73/864.33 |
| 2014/0340099 A1 | 11/2014 | Butterworth et al. | |

(Continued)

FOREIGN PATENT DOCUMENTS

JP 2003014866 A * 1/2003

*Primary Examiner* — David M Schindler
(74) *Attorney, Agent, or Firm* — Standley Law Group LLP; Jeffrey S. Standley; Stephen L. Grant

(57) ABSTRACT

An apparatus (1) for detecting metal is equipped with at least one test device (2) with a non-metallic guide tube (21). Only a proximal end of the guide tube is connected to a pneumatic control unit (3). A distal end of the guide tube has at least one first ventilation port (211). A test article (7), having a known mass of metal, is movable back and forth between the proximal end and the distal end of the guide tube, at least through a section of an electromagnetic field, to verify operation of the metal detection The pneumatic control unit can use air pressure, either elevated above or reduced below the ambient pressure, applied to the proximal end of the guide tube in order to drive the test article back and forth, or only in one direction if it is returned by gravitational force.

17 Claims, 6 Drawing Sheets

(56) References Cited

U.S. PATENT DOCUMENTS

2015/0061654 A1* 3/2015 Onodera ................ B60T 7/042
                                                    324/207.21
2016/0033305 A1* 2/2016 Mehnert .............. G01D 5/2216
                                                    324/207.18

* cited by examiner

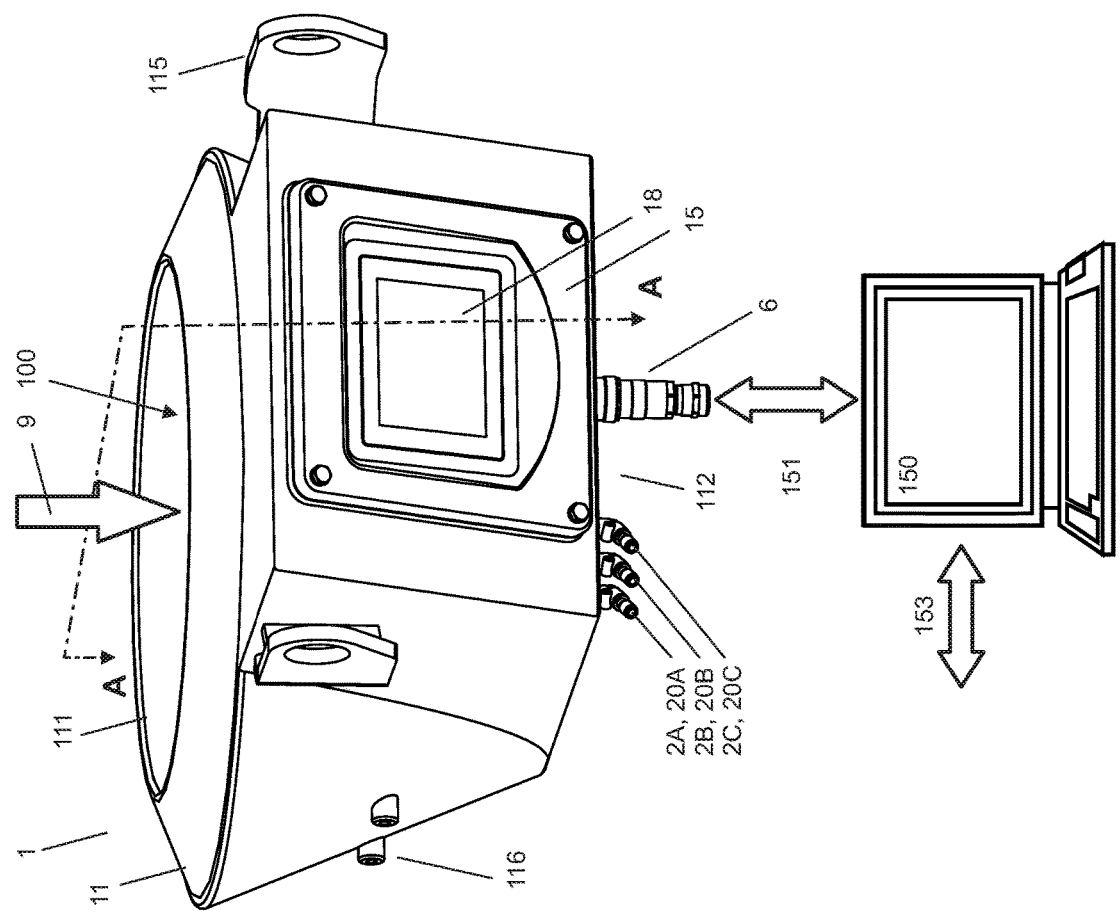
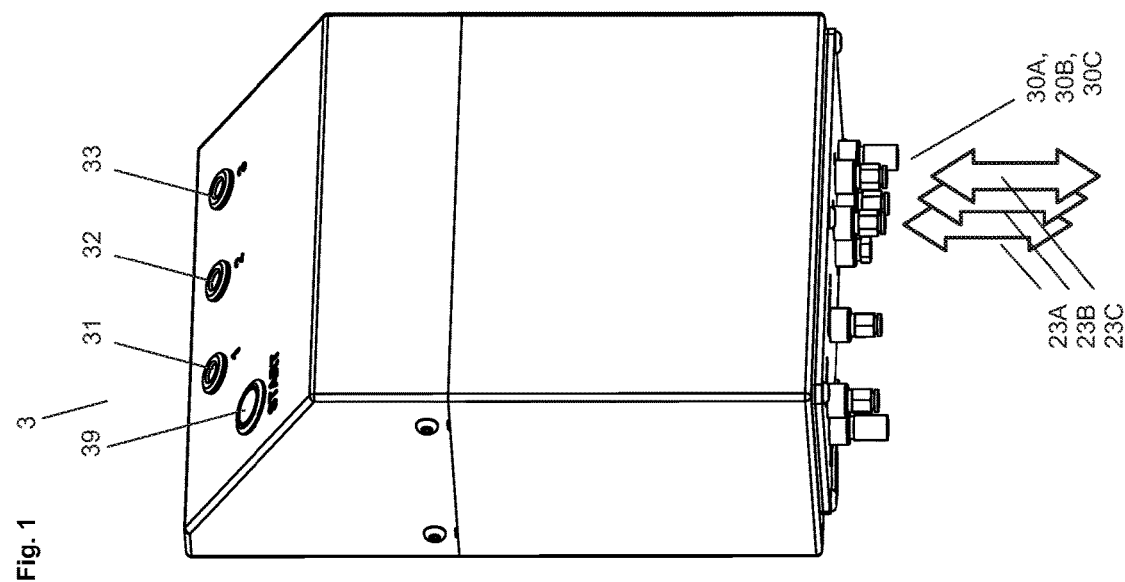
Fig. 1

METAL DETECTION APPARATUS, TESTING DEVICE AND METHOD FOR OPTIMISING A METAL DETECTION APPARATUS

CROSS-REFERENCE TO RELATED APPLICATIONS

This application claims priority under 35 USC 119 to European patent application EP 15 200 786.0, filed on 17 Dec. 2015, the content of which is incorporated by reference as if fully recited herein.

TECHNICAL FIELD

The invention relates to a metal detection apparatus, a device for testing a metal detection apparatus and method for optimising a metal detection apparatus, which is equipped with a test device.

BACKGROUND

A metal detection apparatus is used to detect and reject unwanted metal contamination. When properly installed and operated, it will help reducing metal contamination and improving food safety. Most modern metal detectors utilise a search head comprising a "balanced coil system". Detectors of this design are capable of detecting all metal contaminant types including ferrous, nonferrous and stainless steels in a large variety of products such as fresh and frozen products.

The metal detection apparatus typically comprises a metallic enclosure, having entrance and exit apertures with cross-sectional areas of different or equal size defining a travel path inside the enclosure along which an object under inspection moves.

A metal detection apparatus that operates according to the "balanced coil"-principle typically comprises three coils that are wound onto a non-metallic frame or yoke. The coil system comprises at least one transmitter coil and at least one first and at least one second receiver coil; the respective receiver coils bounding a detection zone inside the enclosure between the entrance and exit apertures. The detection zone has a cross-sectional profile that varies or is constant along the travel path. Systems with cylindrical detection zones typically use coils having identical dimensions with the transmitter coil centred between the two receiver coils. Systems with conical detection zones use coils that differ in size from one another typically with the transmitter coil being off-centred between the two receiver coils. In both systems the coils are arranged such that, when the at least one transmitter coil is energized by an alternating electric current, the electromagnetic field generated thereby induces a first voltage in the first receiver coil and a second voltage in the second receiver coil, the first and second voltages cancelling each other out when there is no metal present in the object under inspection.

As a particle of metal passes through the coil arrangement, the high frequency field is disturbed first near one receiver coil and then near the other receiver coil. While the particle of metal is conveyed through the receiver coils the voltage induced in each receiver coil is changed. This change in balance results in a signal at the output of the receiver coils that can be amplified, processed and subsequently be used to detect the presence of the metal contamination.

The signal processing channels typically split the received signal into two separate components that are 90° apart from one another. The resultant vector has a magnitude and a phase angle, which is typical for the products and the contaminants that are conveyed through the coil system. In order to identify a metal contaminant, "product effects" need to be removed or reduced. If the phase of the product is known then the corresponding signal vector can be reduced. Eliminating unwanted signals from the signal spectrum thus leads to higher sensitivity for signals originating from contaminants.

Methods applied for eliminating unwanted signals from the signal spectrum therefore exploit the fact that the product, the contaminants and other disturbances, have different influences on the magnetic field so that the resulting signals differ in phase.

Distinguishing between the phases of the signal components of different origin by means of a phase detector allows obtaining information about the product and the contaminants. A phase detector, e.g. a frequency mixer or analogue multiplier circuit, generates a voltage signal which represents the difference in phase between the signal input, such as the signal from the receiver coils, and a reference signal provided by the transmitter unit to the receiver unit. Hence, by selecting the phase of the reference signal to coincide with the phase of the product signal component, a phase difference and a corresponding product signal is obtained at the output of the phase detector that is zero. In the event that the phase of the signal components that originate from the contaminants differ from the phase of the product signal component, then the signal components of the contaminants can be detected. However in the event that the phase of the signal components of the contaminants is close to the phase of the product signal component, then the detection of contaminants fails, since the signal components of the contaminants are suppressed together with the product signal component.

In known systems the transmitter frequency is therefore selectable in such a way that the phase of the signal components of the metal contaminants will be out of phase with the product signal component.

WO 2012/045578A1 discloses a method for operating a metal detection system that allows determining a preferable transmitter frequency with which signal components of smallest sized metal particles differ most in phase and amplitude from the phase and amplitude of a product signal.

Hence, for testing and optimising a metal detection apparatus tests with different contaminants need to be performed, which is however time-consuming. Furthermore, tuning should be performed regularly particularly of the changes of the processed product.

U.S. Pat. No. 5,160,885 A discloses a testing device for testing a metal detecting apparatus wherein a test article of representative metal is passed within the coil system through a detection zone for recording a test signal that corresponds to response signals caused by metal particles included in a product travelling through the detection zone. The test article is guided internally in a non-metallic guide tube, which extends through the detection zone from an input aperture to an output aperture of the metal detection apparatus.

The test article is embedded in a slug, which can move freely within the guide tube from one end to the other, and is constrained to move therealong, by pulses of air introduced through the air pipes. Upon the application of pulses of air first through one junction and then through the other junction, the slug will travel from left to right and then from right to left. The test articles can be moved with or without a product simultaneously passing through the detection zone. Hence, at both sides of the metal detection apparatus, end junctions of the tubular guide are connected to pneumatic fittings and pipes.

The guide tube and the pneumatic equipment provided at both ends require considerable space, which is sparsely available in typical metal detection devices. Due to limitations in space, installation of this test device has been avoided for example in metal detection devices, which use conical detection zones.

In food environments, pneumatic elements and fittings of the test device act as dirt traps and require cleaning and maintenance. Further, these items are obstacles and may be subject to accidental damage, e.g. when products are handled.

Further, assembling a metal detection apparatus together with such a test device requires, besides the pneumatic equipment, considerable efforts. Installing the test device into a metal detection apparatus that is already operating in the field is scarcely possible since space is not available for the rather voluminous test device.

U.S. Pat. No. 5,994,897 A discloses a metal detection apparatus which uses the test device disclosed in U.S. Pat. No. 5,160,885 A. A frequency generator, which generates the signal that is supplied to the transmitter coil, is capable of operating on numerous frequencies in the 50 kHz to 2 MHz range. The product is passed through the detector head, with and without the test article present, for each of the operating frequencies. The response signal from the product and the response signal from the product with metal are evaluated for each of the operating frequencies. In this manner the frequency which produces the highest ratio of the signal of the contaminated product compared to the signal of the uncontaminated product can be identified. However, again, this process of optimising the metal detecting apparatus is extremely laborious.

The present invention is therefore based on the object of providing an improved metal detection apparatus that is equipped with an improved test device, the improved test device and an improved method for optimising the metal detection apparatus.

SUMMARY

The above and other objects of the present invention are achieved by an improved metal detection apparatus, a test device for the metal detection apparatus, and a method for optimisation of the metal detection apparatus.

The metal detection apparatus comprises an enclosure, having entrance and exit apertures that define a travel path on the inside of the enclosure, along which objects under inspection are movable, and a coil system, comprising at least one transmitter coil and at least one first and at least one second receiver coil bounding a detection zone inside the enclosure between the entrance and exit apertures. The transmitter and receiver coils are positioned and dimensioned, such that, when the transmitter coil is energized by an alternating electric current, the electromagnetic field generated thereby induces a first voltage in the first receiver coil and a second voltage in the second receiver coil, the first and second voltages cancelling each other out when there is no metal present in the object under inspection.

Between the entrance and exit apertures, which exhibit cross-sectional areas of equal or different size, a yoke is installed that has a cross-sectional profile that is constant or varies along the travel path of the objects under inspection and that supports the coil system.

According to the invention the apparatus is equipped with at least one test device, which comprises a non-metallic guide tube that is connected on a proximal end only to a pneumatic control unit, that exhibits on a distal end at least one ventilation port and that contains a test article, which is movable forth and back between the proximal end and the distal end of the guide tube at least through a section of the electromagnetic field. The pneumatic control unit is capable of applying air pressure, which is elevated or reduced relative to the ambient pressure, to the proximal end of the guide tube in order to drive the test article forth and back or only in one direction if it is returned by gravitational force.

As an example, pressure can be applied to the guide tube moving the test article upwards and letting it fall again by gravitational force when the pressure is removed. Alternatively, a vacuum can be applied to the guide tube for lifting the test article and letting it fall again by gravitational force when the vacuum is removed. The article can also be driven forth and back by selectively applying vacuum or pressure. In all variations pressure or vacuum is applied at the proximal end of the guide tube only. I.e., the pneumatic control unit is connected to the proximal end of the guide tube only, but not to the distal end.

The test device can therefore advantageously be mounted on one side of the metal detection apparatus only with the guide tube extending with its distal end to or beyond the first or second receiver coil. Since the magnetic field is spread out at the inner and outer side of the transmitter and receiver coils the guide tube can be arranged inside or outside of the transmitter and receiver coils preferably in the vicinity of the coil wire. Installing the at least one test device outside the transmitter and receiver coils leaves the detection zone inside the transmitter and receiver coils free for the transferred objects, e.g. food products, while the magnetic field still gets imbalanced when the test article is moving along the coil system.

Due to the reduced space requirements and particularly by avoiding a guide tube that completely traverses the apparatus from one aperture to the other the inventive test device can be installed in any type of metal detection apparatus, including metal detection apparatuses having conical detection zones.

The test sample is moved between the proximal end and the distal end of the guide tube, where it is stopped by an end stop, which preferably comprises the form of a screw or plug that is seated within the guide tube. In the embodiment of a screw, the end stop allows adjusting the path length, along which the test article travels. In the event that a plurality of test devices with different test articles is used, then the end stops can be aligned. Further, the end stop prevents dust particles from entering the first guide tube thus creating obstacles along the travel path of the test article.

In preferred embodiments the movements of the test articles are controlled with respect to acceleration, speed and travel distance. E.g. by applying a specific pressure for a short period of time followed by applying a vacuum the movement of the test article can be fully controlled.

For the free or controlled movement of the test article inside the guide tube it is important that the airway resistance at the ventilation port is constant and preferably low. Hence, in preferred embodiments the test device is provided with a ventilation tube that is connected with one end to the distal end of the guide tube and routed with the other end preferably to the outside of the apparatus. Hence, during operation of the test article air that escapes or enters the guide tube can move freely through the ventilation tube between the distal end of the guide tube and the outside of the apparatus.

In a particularly advantageous embodiment the guide tube is held coaxially aligned within the ventilation tube and is connected with its distal end to a distal end of the ventilation tube that comprises an inner diameter that is larger than the outer diameter of the guide tube. Thus, a hollow cylindrical space results between the guide tube and the ventilation tube, through which air can freely move between the first ventilation port located at the distal end of the guide tube and at least one second ventilation port provided at a proximal end of the ventilation tube.

The connection between the distal end of the guide tube and the distal end of the ventilation tube is preferably established with a bearing element that is seated on the distal end of the ventilation tube and that holds the distal end of the guide tube concentrically within the distal end of the ventilation tube and prevents dust particles from entering the ventilation tube.

The test device is installed in such a way that the proximal end of the guide tube, which is connected to a fitting, is preferably located near the exit aperture of the apparatus, where the inspected objects leave the detection zone. The enclosure is preferably connected to a mounting block, which holds the test devices. The mounting block preferably comprises mounting bores, in which the guide tube or the ventilation tube of the related test device is held. Optionally the fitting at the proximal end of the guide tube is connected to the mounting block. One or a plurality of fittings can also advantageously be incorporated in the mounting block. Preferably an annular mounting block is provided, which surrounds the input aperture or most preferably the exit aperture.

In preferred embodiments, a fitting is provided at the proximal end of the guide tube that holds the proximal end of the ventilation tube at least approximately concentrically to the proximal end of the guide tube. This coaxial alignment of the guide tube and the ventilation tube leads to a compact design of the test device, which can be manufactured in small dimensions. However, the invention is not limited to this ideal arrangement. The guide tube and the ventilation tube could for example also be arranged aligned in parallel next to one another. E.g., a U-shaped tube could be used that combines the guide tube and the ventilation tube. It would also be possible to combine two guide tubes in a U-shaped form with test articles that are simultaneously moving forth and back in each of the U-segments.

The test article is selected as required and preferably consists of or comprises a ferrous or nonferrous material, such as steel, stainless steel, brass or aluminium. In order to ensure smooth and controlled gliding the test article is preferably embedded in a non-metallic carrier or slug. The guide tube and the ventilation tube are made for example from plastic, such as nylon or acryl, which ideally support the slug.

Since the inventive device requires little space it can advantageously be installed in any metal detection apparatus having a cylindrical or conical or other detection zone. Furthermore, a plurality of test devices or a test device with a plurality of guide tubes, preferably guide tubes connected to individual ventilation tubes or a common ventilation tube, can advantageously be installed in a metal detection apparatus, allowing automatic execution of tests with various contaminants.

The inventive apparatus can automatically be optimised for all applications and contaminants by sequentially selecting one of the test articles and selecting for each of the test articles sequentially an operating frequency out of a set of predetermined operating frequencies and moving the selected test article through a section of the electromagnetic field while observing changes of the electromagnetic field. These tests may automatically perform while products are passing through the metal detection apparatus. Hence, optimised operating frequencies can automatically be obtained within short periods of time for all contaminants of interest, for which test articles are provided in the test devices.

BRIEF DESCRIPTION OF THE DRAWINGS

Some of the objects and advantages of the present invention have been stated, others will appear when the following description is considered together with the accompanying drawings, in which:

FIG. 1 shows an inventive metal detection apparatus 1 that is equipped with three test devices 2A, 2B, 2C, which are connected to a pneumatic control device 3;

DETAILED DESCRIPTION

Figure 2:
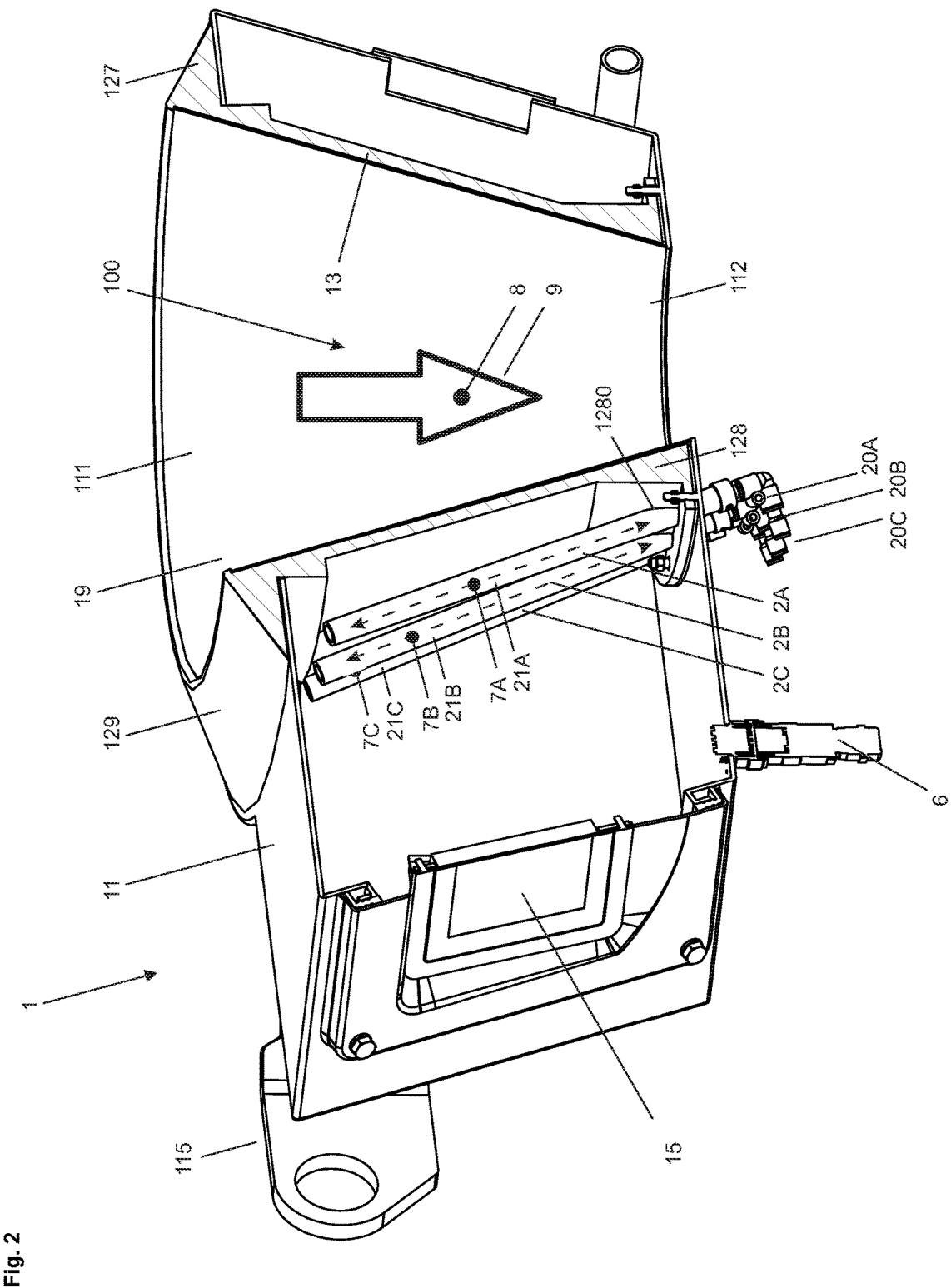
FIG. 2 shows a sectional view of the metal detection apparatus 1 that has been cut along line A-A shown in FIG. 1.

FIG. 1 shows an inventive metal detection apparatus 1 that is equipped with three test devices 2A, 2B, 2C, which are connected to a pneumatic control device 3 as symbolically indicated by arrows.

The metal detection apparatus 1 is designed to detect metal contaminated product in vertical packaging applications, i.e. for the inspection of in-flight product prior to insertion into sealed packs. The apparatus is designed for minimised height allowing it to be installed for example in a restricted space between weigher and bag maker.

The metal detection apparatus 1 comprises an enclosure 11, having entrance and exit apertures 111, 112, which define a travel path inside the enclosure 11 along which objects under inspection 9 can be moved through a detection zone 100. For mounting the metal detection apparatus 1 the enclosure 11 is provided with mounting means such as mounting flanges 115 and mounting bores 116.

The metal detection apparatus 1 is equipped with a local control unit 15 that comprises a display 18 and that is preferably connected via a cable port 6 and a first control bus 151 to a main computer 150. The metal detection apparatus 1 may operate autonomously or under the control of the main computer 150, which may control one or a plurality of metal detection apparatuses 1 and may provide application parameters and gather measurement results.

In order to test and/or optimise the metal detection apparatus 1, it is equipped with three test devices 2A, 2B, 2C, which are mounted on the lower side of the enclosure 11 near the exit aperture 112 and which comprise fittings 20A, 20B, 20C which are connected via pneumatic lines 23A, 23B, 23C, e.g. air hoses, to fittings 30A, 30B, 30C provided at the pneumatic control device 3.

The pneumatic control device 3 preferably comprises pneumatic devices such as pressure generators, vacuum generators and valve means (not shown) which may be operated manually or under the control of the local control device 15 or the main computer 150 via a second control bus 153. The pneumatic control device 3 may comprise for example one or more air pumps and/or one or more vacuum generators operating for example according to the venture principle. The pressure and vacuum generators are preferably equipped with control or switching means for allowing pulsed application of a specific pressure or vacuum. Pneumatic equipment and devices for controlling this pneumatic equipment are available e.g. from Festo AG. The publication "Partnership—with added value" published by Festo discloses products in the range of pneumatics and electrical engineering, with control systems and controllers in a control level and pneumatic, servo pneumatic, electric items in a field level, such as actuators, drives, valves, vacuum generators, motors, and connection technology with tubing, fittings, pneumatic couplings. The pneumatic control device 3 is designed to provide pressure or vacuum preferably in pulses to the pneumatic lines 23A, 23B and 23C in selected test intervals, e.g., every 15 or 30 minutes.

The pneumatic control device 3 may be operated manually by selecting a test device 2A, 2B or 2C by pushing one of the related buttons 31, 32, 33 and by pushing button 39 for starting a test with the selected test device 2A, 2B or 2C. However, test suites are preferably provided and automatically executed by the main computer 150.

FIG. 2 shows a sectional view of the metal detection apparatus 1 that has been cut a long line A-A shown in FIG. 1. It is shown that between the entrance and exit apertures 111, 112, which have cross-sectional areas of different size, a yoke 13 is arranged that has a cross-sectional profile, which varies along the travel path of the objects under inspection 9. The yoke 13, which is held near the exit aperture 112 by a mounting block, preferably an annular mounting block or first mounting ring 128 and near the input aperture supports 111 by a second mounting ring 127, is embraced by a coil system with at least one transmitter coil arranged between at least two receiver coils. The coil system is designed and arranged in such a way that signals supplied to the transmitter coil generate identical signals in the receiver coils, which therefore cancel out if no contamination 8 is present in the product 9. It is symbolically shown that the passing product 9 contains a metal element 8 that causes a signal change first in the first receiver coil and then in the second receiver coil and thus causes an imbalance in the coil system and the related electromagnetic fields.

Within the yoke 13 a funnel 19 is held that guides vertically falling products from its input to its output.

In this sectional view, it is shown, that the three test devices 2A, 2B, 2C are mounted and held in an annular mounting block, namely the first mounting ring 128, which is seated on the enclosure 11 surrounding the exit aperture 112.

The test devices 2A, 2B, 2C comprise each a guide tube 21A, 21B, 21C, which is held in a mounting bore 1280 provided in the annular mounting block 128, which extends with the distal end into the metal detection apparatus 1, which is connected on the proximal end to a fitting 20A, 20B, 20C held outside the metal detection apparatus 1 below the exit aperture 112 and which includes a test article 7A, 7B, 7C. It can be seen that the test devices 2A, 2B, 2C can easily be mounted in the mounting bores 1280 of the annular mounting block 128, e.g. by a press fitting, next to one another in a high number.

The guide tubes 21A, 21B, 21C are arranged on the outside of the conical yoke 13 preferably aligned each in parallel to a generatrix of the conical yoke 13. Hence, test devices 2A, 2B, 2C, . . . can easily be mounted in high numbers within the metal detection apparatus 1 without interfering with the detection zone 100 and without using space on the upper side of the metal detection apparatus 1. Test devices 2A, 2B, 2C can therefore easily be retrofitted in apparatuses 1 which are already operating in the field without this test option.

By the application of air pressure or vacuum, preferably pulses of air pressure or vacuum to the fittings 20A, 20B, 20C the test articles 7A, 7B, 7C, which are preferably embedded in a slug 28 (see FIG. 3B), can individually be moved up and down in the related guide tube 21A, 21B, 21C. The test articles 7A, 7B, 7C can be moved up by the application of air pressure and be returned by gravitational force or the application of vacuum.

The test devices 2A, 2B, 2C preferably comprise different test articles 7A, 7B, 7C that consists of or comprises a ferrous or nonferrous material, such as steel, stainless steel, brass or aluminium. The first test article 7A may consist of steel, the second test article 7B may consist of brass and the third test article 7C may consist of aluminium. Tests may therefore be run for all of these materials with or without a product 9 passing through the detection zone 100. For each selected test article 7A or 7B or 7C tests can be executed manually or automatically preferably for a predetermined number of operating frequencies. Based on the tests the operating frequency or operating frequencies are selected with which the best results or the strongest response signals have been obtained.

Since these tests can automatically be executed it is possible to optimise the test parameters within a short period of time. Preferably, the sequences for testing and optimising the metal detection apparatus 1 are performed in intervals. Operation tests can be made within short intervals of e.g. 15 or 30 minutes. Optimisation sequences are run e.g. in the morning and in the afternoon or always, when significant product changes have occurred.

FIG. 2 shows that the test devices 2A, 2B, 2C do not extend to the upper side of the metal detection apparatus 1, where a closure ring 129 is mounted above the second mounting ring 127. This closure ring 129 and the second mounting ring 127 are free from any parts of the test devices 2A, 2B, 2C. Hence, no dirt traps are present on the upper side of the metal detection apparatus 1. Food particles that are distributed on top of the metal detection apparatus 1 across the second mounting ring 129 can easily be removed.

The test devices 2A, 2B, 2C are not prone to accidental damage when products 9 are handled above the metal detection apparatus 1 or when cleaning the metal detection apparatus 1. In addition to the advantages in operation and maintenance, further advantages relate to the reduction of manufacturing efforts by avoiding tubes and fittings for the test devices 2A, 2B, 2C on the upper side of the metal detection apparatus 1.

Although the guide tubes 21A, 21B, 21C do not extend to the upper side of the metal detection apparatus 1, the individual test articles 7A, 7B, 7C can still pass by the complete coil system. In certain applications it may even be sufficient if the test articles 7A, 7B, 7C are elevated up to the lower second receiver coil.

Figure 3:
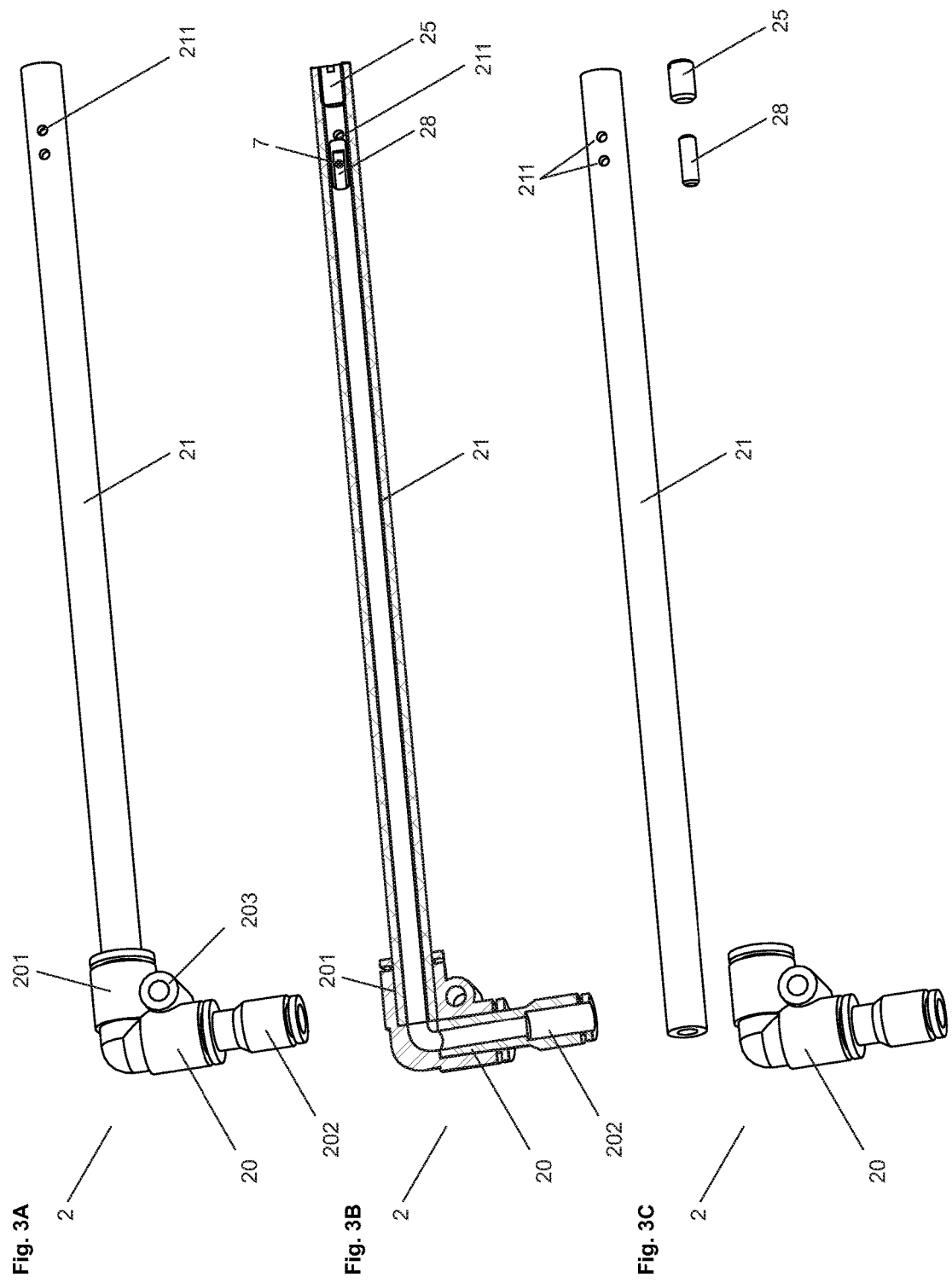
FIG. 3A shows an inventive test device 2 that comprises a guide tube 21 that is connected to a fitting 20 and that encloses a test article 7 embedded in a slug 28 as shown in FIG. 3B.
FIG. 3B shows a sectional view of the test device 2 of FIG. 3A that has been cut in a plane along the centre axis of the guide tube 21 and the fitting 20.
FIG. 3C shows the test device of FIG. 3A in explosion view.

FIG. 3A and FIG. 3B show an inventive test device 2 in spatial view and in sectional view. FIG. 3C shows the test device 2 of FIG. 3A in exploded view. The test device 2 comprises a hollow cylindrical guide tube 21 that at the proximal end is connected to a fitting 20 and that encloses a test article 7 embedded in a slug 28. At the distal end the guide tube 21 is provided with a ventilation port 211 having two exhaust holes and with a threading, into which an end stop 25 is inserted, which may be a threaded bolt. The end stop 25 acts as end stop for the slug 28 and can preferably be adjusted in order to reach a desired length of the travelling path of the slug 28. The angular fitting 20 comprises a first fitting part 201, in which the guide tube 21 is held, and a second fitting part 202, which can be connected to a pneumatic coupling or directly to an air hose. By the application of air pressure, vacuum or gravitational force, the slug 28 can be moved forth and back between the proximal end and the distal end of the guide tube 21. The invention could also be implemented with another gas or a fluid.

Figure 4:
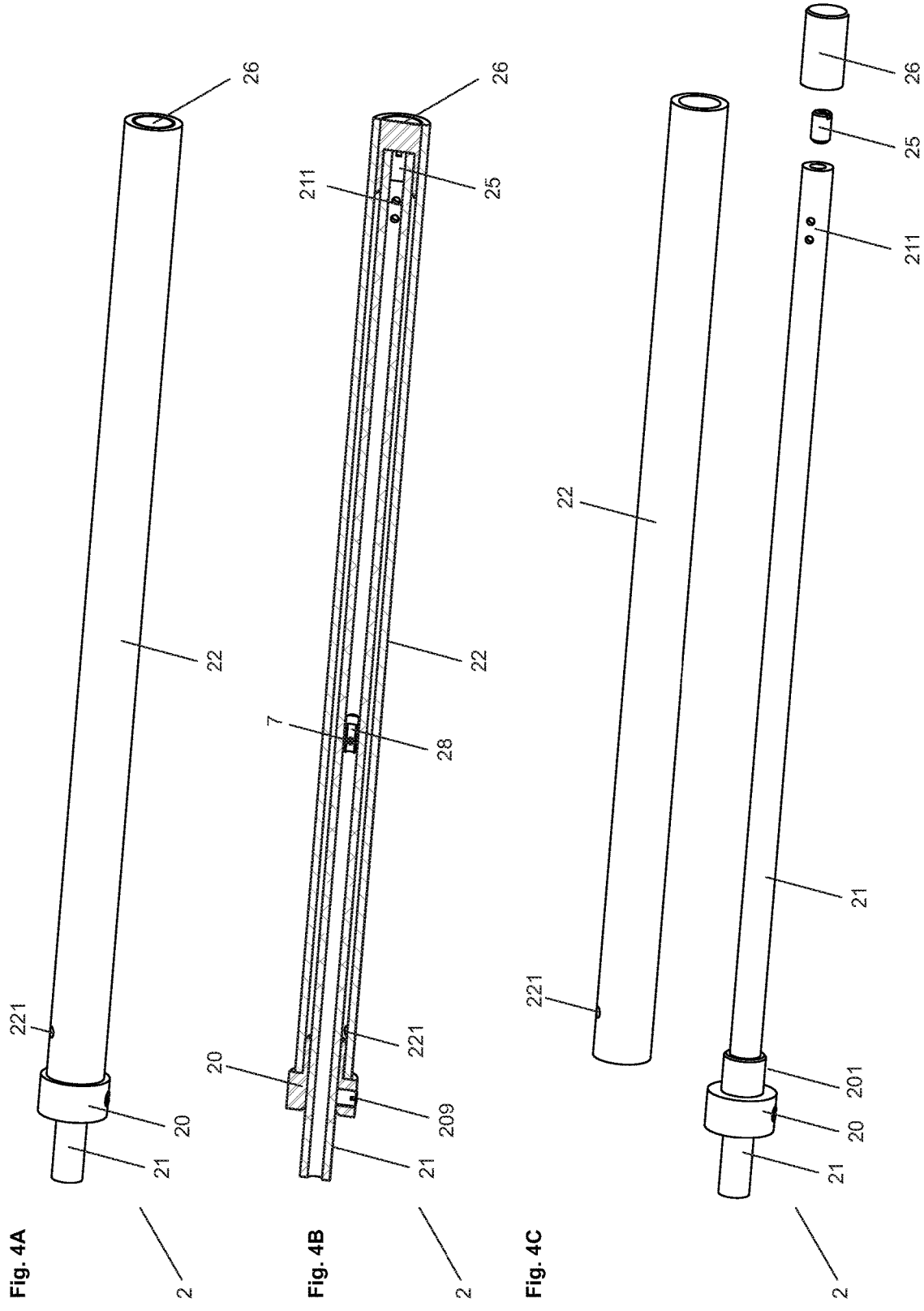
FIG. 4A shows a further inventive test device 2 that comprises a guide tube 21 that is connected to a fitting 20, that encloses a test article 7 embedded in a slug 28 as shown in FIG. 4B and that is held within a ventilation tube 22.
FIG. 4B shows a sectional view of the test device 2 of FIG. 4A that has been cut in a plane along the centre axis of the guide tube 21 and the fitting 20.
FIG. 4C shows the test device of FIG. 4A in explosion view.

FIG. 4A and FIG. 4B show a further inventive test device 2 in spatial view and sectional view. FIG. 4C shows the test device 2 of FIG. 4A in explosion view. This test device 2 comprises also a hollow cylindrical guide tube 21 that at the proximal end is connected to a fitting 20 and that encloses a test article 7 embedded in a slug 28. At the distal end the guide tube 21 is also provided with a ventilation port 211 having two exhaust holes and with a threading, into which an end stop 25 in the embodiment a threaded bolt has been turned. In this embodiment, the fitting 20, which is fully traversed by the guide tube 21 and fixed to the guide tube 21 by a lock screw 209, comprises only a first fitting part 201. On the distal end of the guide tube 21 a cylindrical bearing element 26 is seated that comprises a central bore along its longitudinal axis, which bore receives the distal end of the guide tube 21 without covering the exhaust holes of the first ventilation port 211.

On the first fitting part 201 of the fitting 20 and on the bearing element 26 the proximal and distal ends of a hollow cylindrical ventilation tube 22 are seated coaxially aligned with the guide tube 21 so that the distal ends and at least partly the proximal ends of the guide tube 21 and the ventilation tube 22 overlap. The ventilation tube 22 comprises a ventilation port 221 at the proximal end close to the fitting 20. The ventilation tube 22 comprises an inner diameter that is larger than the outer diameter of the guide tube 21 thus providing a hollow cylindrical ventilation space between the guide tube 21 and the ventilation tube 22, through which air is movable between the first ventilation port 211 located at the distal end of the guide tube 21 and the second ventilation port 221 provided at the proximal end of the ventilation tube 22. This arrangement of the guide tube 21 and the ventilation tube 22 allows free air flow forth and back, when the test device 2 is operated and the slug 28 is moved between the proximal end and distal end of the guide tube 21. Although an additional air path outside the guide tube 21 has been created the dimensions of the test device 2 are only slightly increased. Hence, also in this embodiment, in which, except for the movable slug 28, an unhindered airflow from the outside of the metal detection apparatus 1 through the guide tube 21 and the ventilation tube 22 back to the outside of the metal detection apparatus 1 is established, the test device 2 requires little space and can easily be installed in any type of metal detection apparatus 1.

Figure 5:
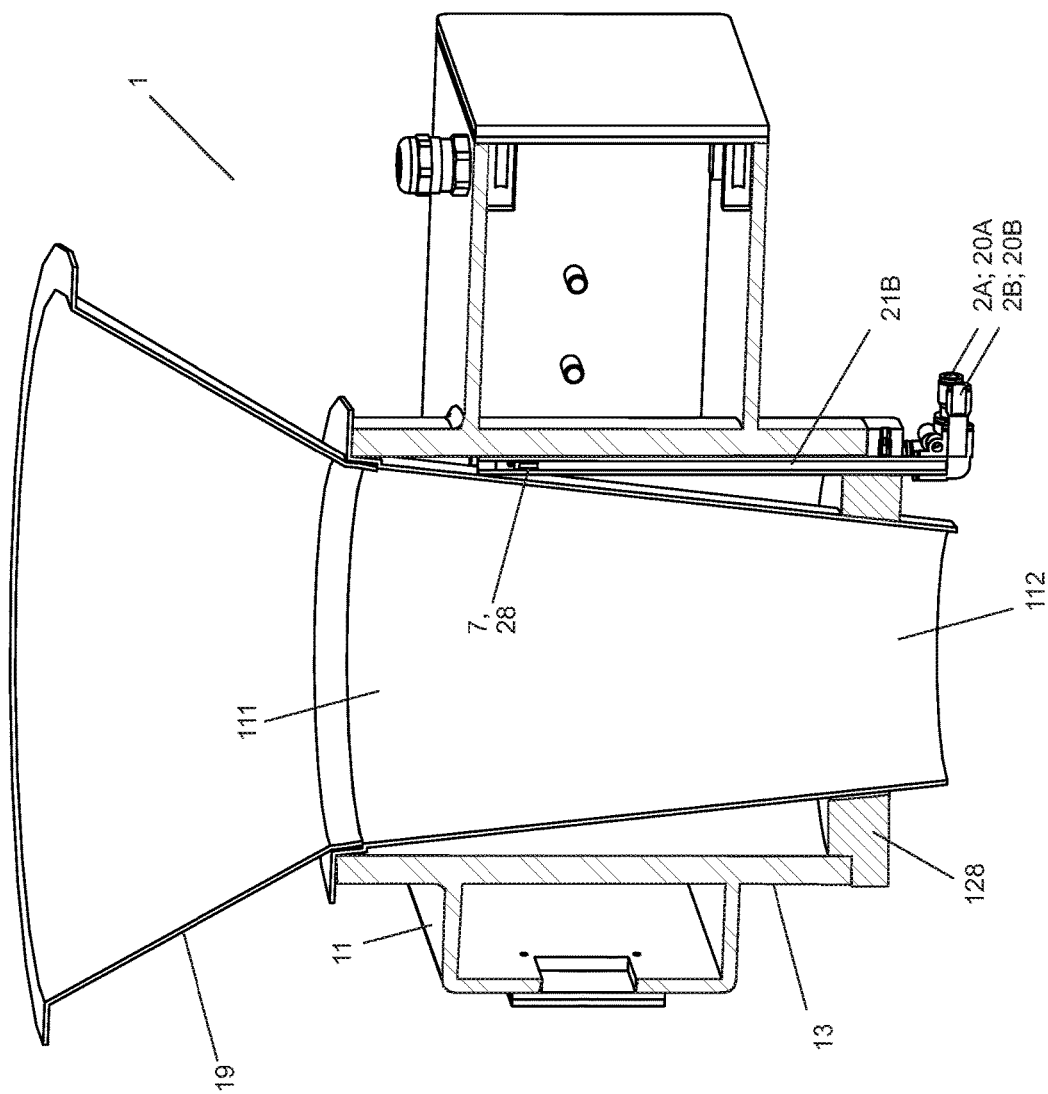
FIG. 5 shows in sectional view an inventive metal detection apparatus 1 that comprises a hollow cylindrical yoke 13 with a funnel 19 that has been inserted from above through the first aperture 111 and with test devices 2A, 2B, that have been inserted through the second aperture 112.

FIG. 5 shows in sectional view an inventive metal detection apparatus 1 that comprises a hollow cylindrical yoke 13 with a funnel 19 that has been inserted from above through the first aperture 111 and with test devices 2A, 2B, that have been inserted through the second aperture 112. The funnel 19 completely fills the first aperture 111 and does not allow mounting any test devices or parts thereof near the first aperture 111. Consequently, the test devices of the prior art, as described above, could not be installed in this embodiment of the metal detection apparatus 1.

Instead the inventive test device 2 does not require much space and can be mounted on a side of the metal detection apparatus 1, where free space is available. Since the guide tubes 21A, 21B, . . . , of the test devices 2A, 2B, . . . , do not need to completely traverse the yoke 13 they can easily be mounted on one side.

The mounting ring 128, which holds the lower side of the conical funnel 19, is provided with bores, through which the guide tubes 21A, 21B, . . . , of the test devices 2A, 2B, . . . , are inserted. This can be done during production of the metal detection apparatuses 1 or in the field at metal detection apparatuses 1 that are already in operation. The form of the mounting ring or mounting means 128 shown in FIG. 5 is an example only. Mounting means 128 could also be rectangular or simply a flange element that is part of or connected to an element of the metal detection apparatus, e.g. the enclosure 11 or the yoke 13.

In the embodiment of FIG. 5, the guide tubes 21A, 21B, . . . , of the test devices 2A, 2B, . . . , are held within the yoke 13, which supports the coil system (not shown). Hence, inventive test devices 2 can be mounted inside or outside of a yoke and a coil system connected thereto. Furthermore, inventive test devices 2 can be used practically with any kind of yoke or metal detection apparatus. Inventive test devices 2 can be mounted and used particularly in metal detection apparatuses arranged for the inspection of goods that are vertically falling through the coil system or that are transported by a conveyor horizontally through the coil system.

Figure 6:
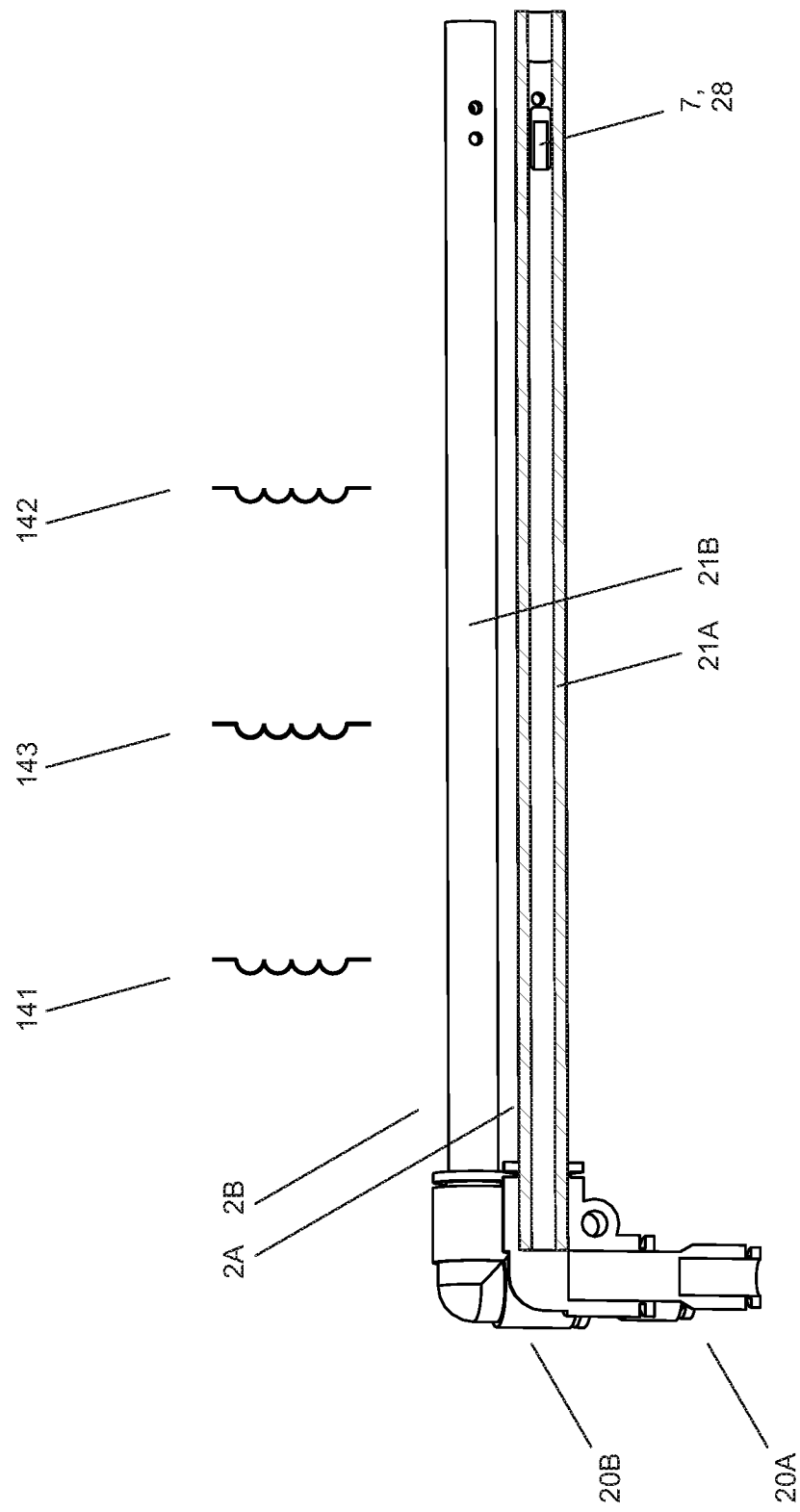
FIG. 6 shows the test devices 2A, 2B of FIG. 5 and symbolically a coil system that comprises a transmitter coil 143 arranged between two receiver coils 141, 142.

FIG. 6 shows the test devices 2A, 2B of FIG. 5, test device 2A in sectional view, and symbolically a coil system that comprises a transmitter coil 143 arranged between two receiver coils 141, 142. The coil system 141, 142, 143 is designed and arranged in such a way that signals supplied to the transmitter coil 143 generate identical signals in the receiver coils 141, 142, which therefore cancel out if no contamination 8 is present in the product 9 that is moved through the coil system and no test article 7 is moved through the electromagnetic field induced in the receiver coils 141, 142. For this purpose, the test articles 7 can be transferred within or outside the transmitter and receiver coils 141, 142, 143.

What is claimed is:

1. An apparatus for detecting metal in an object under inspection, the apparatus comprising:
   an enclosure with an entrance aperture and an exit aperture that define, inside the enclosure, a travel path along which the object under inspection moves;
   a coil system, comprising:
      at least one transmitter coil, energized by an alternating electric current provided by a source; and
      at least one first and at least one second receiver coil, the respective receiver coils bounding a detection zone inside the enclosure between the respective apertures, the respective coils positioned and dimensioned, such that an electromagnetic field generated by the at least one transmitter coil induces a first voltage in each first receiver coil and a second voltage in each second receiver coil, the first and second voltages cancelling each other out when no metal is present in the object under inspection;
   a pneumatic control unit; and at least one test device, the at least one test device comprising at least one non-metallic guide tube with proximal and distal ends, the at least one test device configured at only the proximal end thereof for connection to the pneumatic control unit, the at least one test device having at least one first ventilation port at the distal end, the at least one test device containing a test article, the pneumatic control unit configured to move the test article within the guide tube between the respective ends thereof through at least a section of the electromagnetic field, the test article consisting of only metal, the movement of the test article within the guide tube accomplished by applying air pressure by way of the pneumatic control unit to the proximal end of the guide tube, with or without an assistance of gravitational force, the air pressure being either elevated above or reduced below to an ambient pressure.

2. The apparatus of claim 1, wherein:
   the distal end of the guide tube is positioned to extend to or beyond the at least one first receiver coil or the at least one second receiver coil, within or outside of the coil system.

3. The apparatus of claim 2, further comprising:
   an end stop, mounted on the distal end of the guide tube, seated in a threading provided inside the guide tube.

4. The apparatus of claim 1, wherein:
   each said test device further comprises a non-metallic ventilation tube, connected to the distal end of the respective guide tube, through which air can move into or out of the respective guide tube.

5. The apparatus of claim 4, wherein:
   the guide tube is aligned coaxially aligned within, and connected to the distal end of, the ventilation tube, an outer diameter of the guide tube being smaller than an inner diameter of the ventilation tube, the ventilation tube providing a ventilation space through which air is movable between the at least one first ventilation port located at the distal end of the guide tube and at least one second ventilation port at a proximal end of the ventilation tube.

6. The apparatus of claim 4, further comprising:
   a bearing element is seated on the distal end of the ventilation tube, holding the distal end of the guide tube concentrically within the distal end of the ventilation tube.

7. The apparatus of claim 4, further comprising:
   a fitting, connected to the proximal end of the guide tube for holding the proximal end of the ventilation tube at least approximately concentrically to the proximal end of the guide tube.

8. The apparatus of claim 7, further comprising:
   a mounting block, arranged to hold the at least one test device.

9. The apparatus of claim 7, wherein:
   each guide tube is connected to the pneumatic control device and guides, through the fitting, the respective test article and is individually connected to the pneumatic control device, or
   each said test device is connected to the pneumatic control device and guides the respective article.

10. The apparatus of claim 1, wherein:
    the test article is metallic and is embedded in a non-metallic slug.

11. The apparatus of claim 4, wherein:
    each guide tube and ventilation tube is made from a polymer.

12. The apparatus of claim 1, further comprising:
    a yoke is arranged between the entrance and exit apertures that supports the coil system.

13. The apparatus of claim 3, wherein:
    the at least one test device further comprises a non-metallic ventilation tube, connected to the distal end of the guide tube, through which air can move into or out of the guide tube.

14. A method for testing a functionality of an apparatus for detecting metal in an object under inspection, a apparatus comprising an enclosure with entrance and exit apertures that define a travel path inside the enclosure along which the object under inspection moves, with a coil system arranged in the enclosure, the coil system having at least one transmitter coil and at least one first receiver coil and at least one second receiver coil, the respective receiver coils bounding a detection zone inside the enclosure between the apertures, the respective coils positioned and dimensioned, so that an electromagnetic field generated by energizing the at least one transmitter coil with alternating current, provided by a source, induces a first voltage in each of the at least one first receiver coils and a second voltage in each of the at least one second receiver coils, where the first and second voltages cancel each other out when no metal is present in the object under inspection, the method comprising the steps of:
   providing a pneumatic control unit and a test device, the test device comprising at least one non-metallic guide tube with proximal and distal ends and being configured at only the proximal end thereof for connection to the pneumatic control unit, the guide tube having at least one first ventilation port at the distal end, the guide tube containing a test article consisting of only metal, the guide tube arranged with a portion thereof in a section of the electromagnetic field and a portion thereof outside the electromagnetic field, the pneumatic control unit configured to move the test article within the guide tube between the respective ends of the guide tube by applying air pressure to the proximal end of the guide tube, with or without an assistance of gravitational force, the air pressure being either elevated above or reduced below to an ambient pressure; generating the electromagnetic field while no said metal is present in the field, to observe a null result; and observing a non-null result, by using the pneumatic control unit to cause the movement of the test article between the respective ends and thus to introduce the test article into the portion of the guide tube in the electromagnetic field and move the test article through the section of the electromagnetic field.

15. The method of claim 14, wherein the observing step is performed a plurality of times, during which an operating frequency of the electromagnetic field and a metallic mass off the test article are varied.

16. The apparatus of claim 3, wherein the end stop is a screw or plug.

17. The apparatus of claim 8, wherein the mounting block is located near the exit aperture.

* * * * *